(12) United States Patent
Zhu et al.

(10) Patent No.: US 11,841,377 B2
(45) Date of Patent: Dec. 12, 2023

(54) COAL AND GANGUE IDENTIFICATION DEVICE AND COAL AND GANGUE SORTING SYSTEM

(71) Applicant: Anhui University of Science And Technology, Huainan (CN)

(72) Inventors: Jinbo Zhu, Huainan (CN); Chao Wang, Huainan (CN); Yongcun Guo, Huainan (CN); Yong Zhang, Huainan (CN); Hongzheng Zhu, Huainan (CN); Wei Zhou, Huainan (CN); Ke Yang, Huainan (CN)

( * ) Notice: Subject to any disclaimer, the term of this patent is extended or adjusted under 35 U.S.C. 154(b) by 134 days.

(21) Appl. No.: 17/506,648

(22) Filed: Oct. 20, 2021

(65) Prior Publication Data

US 2022/0136947 A1    May 5, 2022

(51) Int. Cl.
| | | |
|---|---|---|
| *G01N 9/02* | (2006.01) | |
| *B07C 5/22* | (2006.01) | |
| *B07C 5/36* | (2006.01) | |
| *G01N 33/22* | (2006.01) | |

(52) U.S. Cl.
CPC ............ *G01N 9/02* (2013.01); *B07C 5/22* (2013.01); *B07C 5/361* (2013.01); *G01N 33/222* (2013.01)

(58) Field of Classification Search
CPC .......... G01N 9/02; G01N 33/222; B07C 5/22; B07C 5/361; B07C 5/34; B65G 47/52; B65G 47/18; B65G 65/40
See application file for complete search history.

(56) References Cited

U.S. PATENT DOCUMENTS

| | | | | |
|---|---|---|---|---|
| 4,282,088 A | * | 8/1981 | Ennis ................... | B03B 5/36 209/172.5 |
| 4,865,740 A | * | 9/1989 | Callut ................... | B03B 9/005 209/729 |
| 5,108,626 A | * | 4/1992 | Lees ..................... | B07B 1/46 210/780 |
| 5,277,368 A | * | 1/1994 | Kindig .................. | B03B 5/30 209/172.5 |
| 5,348,160 A | * | 9/1994 | Kindig .................. | B03B 5/30 252/60 |
| 11,453,032 B2 | * | 9/2022 | Guo ...................... | B07B 1/14 |
| 2014/0291213 A1 | * | 10/2014 | Chen ..................... | B07C 5/367 209/44.2 |
| 2015/0314332 A1 | * | 11/2015 | Dimitrakis ............ | G01J 5/10 209/11 |
| 2016/0279674 A1 | * | 9/2016 | Kingman ............... | G01N 25/72 |

FOREIGN PATENT DOCUMENTS

CN            101637765 A    *    2/2010

* cited by examiner

*Primary Examiner* — Patrick H Mackey

(57) ABSTRACT

A coal and gangue identification device is disclosed. The device includes a rotary supporting frame, a water injection unit, a weighing unit, a liquid level detection device and a processing module. The rotary supporting frame is provided with a loading unit used to load a mineral aggregate. The rotary supporting frame is used to drive the loading unit to rotate on a horizontal plane. In the rotating process of the rotary supporting frame, the loading unit cyclically passes through a water injection region, a material adding region, a volume measurement region and an unloading region which are sequentially disposed on a rotation trajectory of the rotary supporting frame. The water injection unit is used to inject water to the loading unit of the water injection region.

10 Claims, 9 Drawing Sheets

COAL AND GANGUE IDENTIFICATION DEVICE AND COAL AND GANGUE SORTING SYSTEM

TECHNICAL FIELD

The present invention relates to the field of coal and gangue sorting equipment, in particular to a coal and gangue identification device and a coal and gangue sorting system.

BACKGROUND

Coal gangue is the waste discharged during coal mining, and washing and processing. A photoelectric sorting device is mainly used for current coal and gangue identification. γ rays or X rays used by the photoelectric sorting device have the risk of radiation pollution, so the protective measures will be more complicated, and equipment design and installation will be restrained by a limited underground space.

SUMMARY

In order to solve the defects that the coal and gangue separation device in the prior art strongly depends on the environment and cannot perform underground operations, the present invention provides a coal and gangue identification device and a coal and gangue sorting system.

A first purpose of the present invention uses the following technical solution:

a coal and gangue identification device includes a rotary supporting frame, a water injection unit, a weighing unit, a liquid level detection device, and a processing module;

the rotary supporting frame is provided with a loading unit used to load a mineral aggregate; the rotary supporting frame is used to drive the loading unit to rotate on a horizontal plane; in the rotating process of the rotary supporting frame, the loading unit cyclically passes through a water injection region, a material adding region, a volume measurement region, and an unloading region which are sequentially disposed on a rotation trajectory of the rotary supporting frame; the water injection unit is used to inject water to the loading unit of the water injection region; the weighing unit is used to acquire the weight of the mineral aggregate filled to the loading unit in the material adding region; the liquid level detection device is used to measure a liquid level in the loading unit on the volume measurement region;

the processing module is used to calculate, according to a measurement result of the liquid level detection device, a volume of the mineral aggregate filled to the loading unit, and is used to identify the mineral aggregate in combination with the volume and the weight of the mineral aggregate obtained by the weighing unit; and the processing module is also used to control, according to an identification result, the loading unit to perform unloading in the unloading region.

A second purpose of the present invention uses the following technical solution:

a coal and gangue sorting system includes a coal and gangue sorting device, and the above-mentioned coal and gangue identification device.

The coal and gangue sorting device includes a second conveying belt; a feeding end of the second conveying belt is located below the unloading region; a gangue runner and a clean coal runner are arranged on the second conveying belt side by side; and the processing module of the coal and gangue identification device is used to control, according to an identification result, the loading unit to discharge the mineral aggregate to the clean coal runner or the gangue runner in the unloading region.

The present invention has the advantages that:

(1) In the present invention, the volume of the mineral aggregate is obtained through liquid level measurement, the weight of the mineral aggregate is acquired through the weighing unit, and the mineral aggregate is identified in combination with a weight to volume ratio of the mineral aggregate.

(2) The present invention is simple and practical in structural design, safe, and radiation pollution-free; the management and maintenance difficulty and the industry access standard are greatly reduced; and meanwhile, underground on-site operations can be performed, without the need of transporting the raw coal to the ground, so that the cost of coal and gangue identification is greatly reduced.

Figure 1:
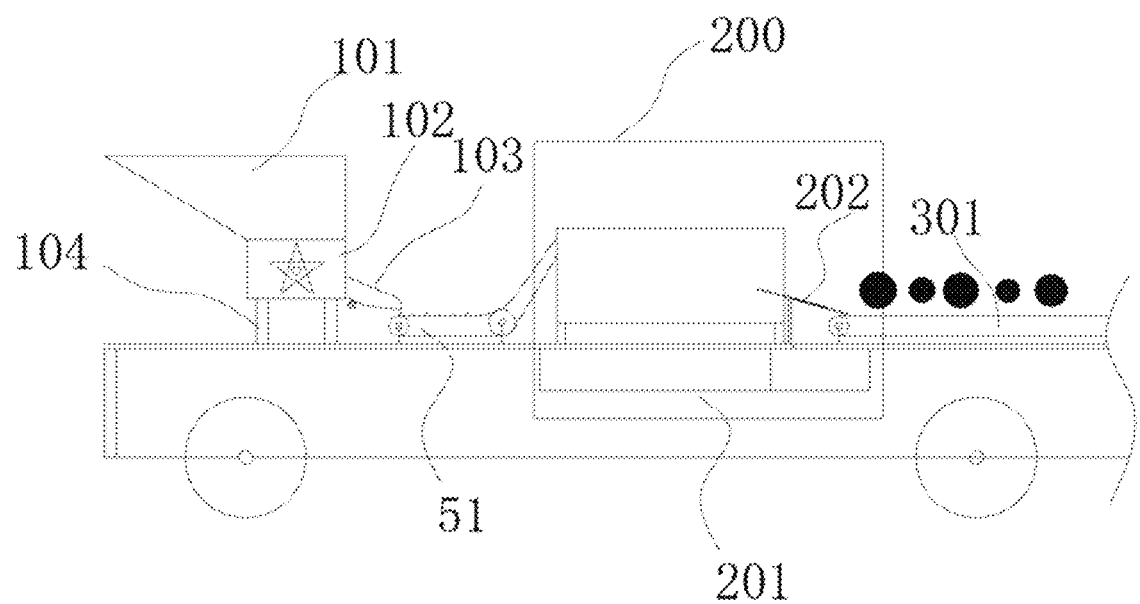
FIG. 1 is a schematic front view of a high-accuracy coal and gangue identification system provided by embodiment 1.

In the drawings; 100: distribution queuing device; 101: receiving hopper; 102: star-type feeder; 103: discharge chute; 104: supporting leg; 105: shock excitation motor; 106: grading screen; 107: sequencing runner; 108: diversion and material separation structure; 200: coal and gangue identification device; 201: circulating water tank; 202: dewatering screen; 211: first barrel body; 212: upper supporting disk; 213: lower supporting disk; 214: first weighing barrel; 215: first liquid level sensor; 216: first weighing sensor; 217: first rotating shaft; 218: axial thrust bearing; 219: first motor; 2110: supporting connection rod; 2111: ring-like overlap edge; 2112: first discharge electromagnetic valve; 2113: first metering pump; 2114: filtration division layer; 20a: water injection region; 20b: material adding region; 20c: volume measurement region; 20d: discharge region; 2011: muddy water chamber; 2012: clean water chamber; 221: balance plate; 222: balance box; 223: triangular fixture; 224: second weighing sensor; 225: second rotating shaft; 226: supporting part; 227: second weighing barrel; 228: second metering pump; 229: second motor; 2210: second liquid level sensor; 2211: water supplementing tank; 2013: overflow slot; 300: coal and gangue tracking unit; 301: third conveying belt; 302: camera; 303: transfer chute; 4110: cantilever grate bar; 411: guide part; 412: gangue collection bin; 413: clean coal collection bin; 414: first supporting seat; 415: cantilever shaft; 4111: first high-pressure nozzle; 4112: first air feed pipe; 4113: first groove; 4114: first air feed electromagnetic valve; 4115: first reset spring; 4116: first push rod; 4121: first pulley; 4122: second push rod; 4123: first extrusion rod; 4124: first hinging connection rod; 4131: fixed rod; 4132: third push rod; 4133: second extrusion rod; 4134: second pulley; 4135: third pulley; 421: separation bracket; 422: fourth conveying belt; 423: fifth conveying belt; 424: deflector rod; 425: second high-pressure nozzle; 426: second air feed electromagnetic valve; 427: second reset spring; 428: second air feed pipe; 429: baffle plate; 4210: second groove; 431: second conveying belt; 432: runner partition plate; 441: transmission chain; 4410: chain slot; 442: sixth conveying belt; 443: seventh conveying belt; 444: second discharge electromagnetic valve; 445: fixed roller; 446: tension roller; 51: first conveying belt; 1: base; 2: wheel; 54: second transportation mechanism.

DETAILED DESCRIPTION OF THE EMBODIMENTS

Embodiment 1: High-Accuracy Coal and Gangue Identification System

Referring to FIG. 1, the present embodiment provides a high-accuracy coal and gangue identification system, including a base 1, a distribution queuing device 100, and a coal and gangue identification device 200.

The distribution queuing device 100 includes a receiving hopper 101, a star-type feeder 102, and a first supporting leg 104.

The star-type feeder 102 is mounted on the base 1 through the first supporting leg 104, and the receiving hopper 101 is arranged on the star-type feeder 102. The top of the receiving hopper 101 is opened, and the bottom of the receiving hopper is provided with a one-piece material outlet and is communicated with a mineral aggregate inlet of the star-type feeder 102. As such, a mineral aggregate in the receiving hopper 101 is discharged by means of the star-type feeder 102, thereby realizing intermittent uniform discharging of the mineral aggregate. In specific implementation, the receiving hopper 101 can also be configured to be a structure with a wider upper part and a narrower lower part to facilitate down sliding of the mineral aggregate.

In the present embodiment, the coal and gangue identification device 200 includes a rotary supporting frame, a water injection unit, a weighing unit, a liquid level detection device, and a processing module. The rotary supporting frame is rotatably mounted on the base 1; the rotary supporting frame is provided with a plurality of loading units; and the plurality of loading units are uniformly distributed in a rotation direction of the rotary supporting frame. Each loading unit at least includes one container used to load liquid and the mineral aggregate.

A water injection region 20a, a material adding region 20b, a volume measurement region 20c, and an unloading region 20d are sequentially arranged on a rotation trajectory of the rotary supporting frame. In the rotation process of the rotary supporting frame, each loading unit cyclically passes through the water injection region 20a, the material adding region 20b, the volume measurement region 20c, and the unloading region 20d.

In the rotation process of the rotary supporting frame, the loading unit is injected with clear water at a certain volume in the water injection region 20a by means of a water injection unit, is filled with a mineral aggregate in the material adding region 20b, and discharges the mineral aggregate and the clear water in the unloading region 20d. The weighing unit is used to acquire the weight of the mineral aggregate filling the loading unit; and the liquid level detection device is used to detect a liquid level value in the loading unit located in the volume measurement region 20c.

The processing module is used to acquire a volume of the clear water injected into the loading unit in the water injection region 20a, the liquid level value detected by the liquid level detection device, and the weight, detected by the weighing unit, of the mineral aggregate in the loading unit, and is used to calculate the volume of the mineral aggregate in the loading unit in combination with the liquid level value and the volume of the clear water and calculate the density of the mineral aggregate in combination with the volume of the mineral aggregate and the weight of the mineral aggregate to determine whether the mineral aggregate is coal or gangue according to the density of the mineral aggregate.

Specifically, the processing module calculates an actual ratio B of coal to gangue in the mineral aggregate in the loading unit according to the following formula model 1.

$$\begin{cases} \rho_1 = \dfrac{1 - m(\rho_{mei} - \rho)}{\rho_{mei}\rho} \\ \rho_2 = \dfrac{1 - n(\rho_{gan} - \rho)}{\rho_{gan}\rho} \\ X + Y = V \\ \rho_1 X + \rho_2 Y = M \\ B = X/Y \end{cases}$$

wherein V is the volume of the mineral aggregate; M is the mass of the mineral aggregate; X is the volume of clean coal contained in the mineral aggregate; Y is the volume of gangue contained in the mineral aggregate; $\rho$ is the density of water; $\rho_{mei}$ is the density of the clean coal; $\rho_{gan}$ is the density of the gangue; m is the moisture content of the clean coal in the mineral aggregate; and n is the moisture content of the gangue in the mineral aggregate.

In the present embodiment, the volume of the clear water injected to the loading unit in the water injection region 20a can be obtained by means of liquid level detection, weighing, etc. Quantitative water injection to the loading unit can be realized in the water injection region 20a by means of a circulating metering pump. In the present embodiment, a container in the loading unit located in the material adding region 20b can be configured to be just located below an output port of the star-type feeder 102, so that a material can be directly fed to the loading unit of the material adding region 20b by means of the star-type feeder 102.

In specific implementation, a first transportation mechanism used to transport the mineral aggregate output by the star-type feeder 102 to the loading unit of the material adding region 20b and fill the mineral aggregate to the container can also be arranged on the base 1. For example, in the present embodiment, the first transportation mechanism includes a discharge chute 103 and a first conveying belt 51. The discharge chute 103 is connected with the output end of the star-type feeder 102; the first conveying belt 51 is arranged between the discharge chute 103 and the rotary supporting frame, and is used to convey the mineral aggregate output by the star-type feeder 102 through the discharge chute 103 to the loading unit of the material adding region 20b. In the present embodiment, the discharge chute 103 is also provided with a shock excitation motor 105 to vibrate the discharge chute 103 to avoid discharge blockage. A shock excitation direction of the shock excitation motor 105 is perpendicular to a conveying direction of the mineral aggregate, thus fully dispersing the mineral aggregate, so that the mineral aggregate orderly enters the discharge chute 103.

In the present embodiment, the first conveying belt 51 uses a partition plate conveying belt, so that the mineral aggregate is input to the loading unit block by block. By means of setting an operating speed and a partition plate spacing of the first conveying belt 51, the mineral aggregate output speed of the first conveying belt 51 can match the rotating speed of the rotary supporting frame to ensure that one block of mineral aggregate corresponds to one loading unit, thereby realizing accurate measurement of the mineral aggregate and avoiding sprinkling of the mineral aggregate.

In specific implementation, in the present embodiment, the star-type feeder 102 can be deleted, so that the receiving hopper 101 directly discharges the mineral aggregate to a first conveying belt; or, the discharge chute 103 is arranged on the receiving hopper 101, so that the receiving hopper 101 uniformly discharges the mineral aggregate to the first conveying belt by means of the discharge chute 103.

In the present embodiment, the coal and gangue identification device 200 further includes a circulating water tank 201 and a dewatering screen 202; the circulating water tank 201 is arranged on the base 1 and is used to supply water to the water injection unit; and the dewatering screen 202 is arranged above the circulating water tank 201 and is located below the loading unit on the unloading region 20d. As such, the water injection unit obtains clear water from the circulating water tank 201 and injects the clear water to the loading unit of the water injection region 20a; the loading unit moves to the unloading region 20d and discharges the materials towards the dewatering screen 202; the dewatering screen 202 separates the mineral aggregate from the clear water; and the clear water returns to the circulating water tank 201 by means of the dewatering screen 202 to realize cyclic use of the clear water. In the present embodiment, the dewatering screen 202 is inclined, so that blanking of the mineral aggregate left on the dewatering screen 202 is facilitated, and the load-bearing risk of the dewatering screen 202 is avoided.

In the present embodiment, the loading units located on the same circumferential rotation trajectory are taken as a loading queue, and correspondingly, the star-type feeder 102 and the loading queue are taken as a weighing mechanism. In specific implementation, a plurality of weighing mechanisms can be disposed side by side. The plurality of weighing mechanisms can be respectively provided with corresponding receiving hoppers, circulating water tanks 201, dewatering screens 202, etc., or can share a receiving hopper, a circulating water tank 201, a dewatering screen 202, etc.

In specific implementation, in the present embodiment, a grading screen 106 used to screen mineral aggregates with different particle sizes is arranged in the receiving hopper 101; the receiving hopper 101 is provided with a plurality of outlets corresponding to the mineral aggregates with different particle sizes; and all the outlets are correspondingly provided with the star-type feeders 102 and the coal and gangue identification devices. As such, the mineral aggregates with different particle sizes are screened and separately conveyed by means of the grading screen 106; all the star-type feeders 102 are used to convey the mineral aggregates discharged from the corresponding outlets of the receiving hopper 101 to the corresponding coal and gangue identification devices or the loading queues for coal and gangue identification, so that all the coal and gangue identification devices are used to identify mineral aggregates at specified particle size grades.

Embodiment 2: Coal and Gangue Identification Device

Figure 2:
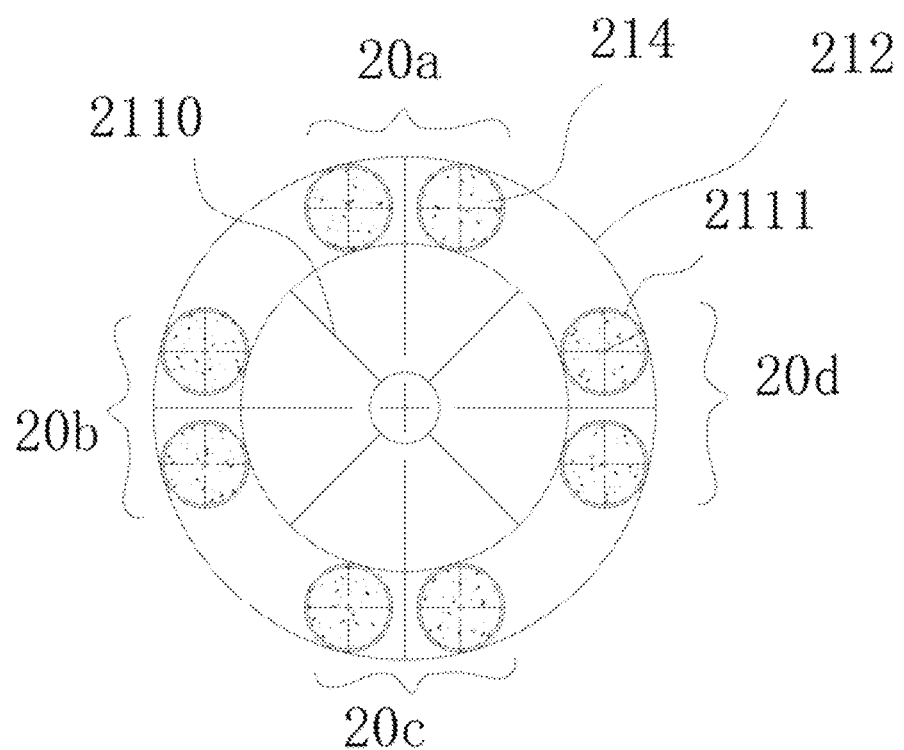
FIG. 2 is a partial top view of a coal and gangue identification device provided by embodiment 2.
Figure 3:
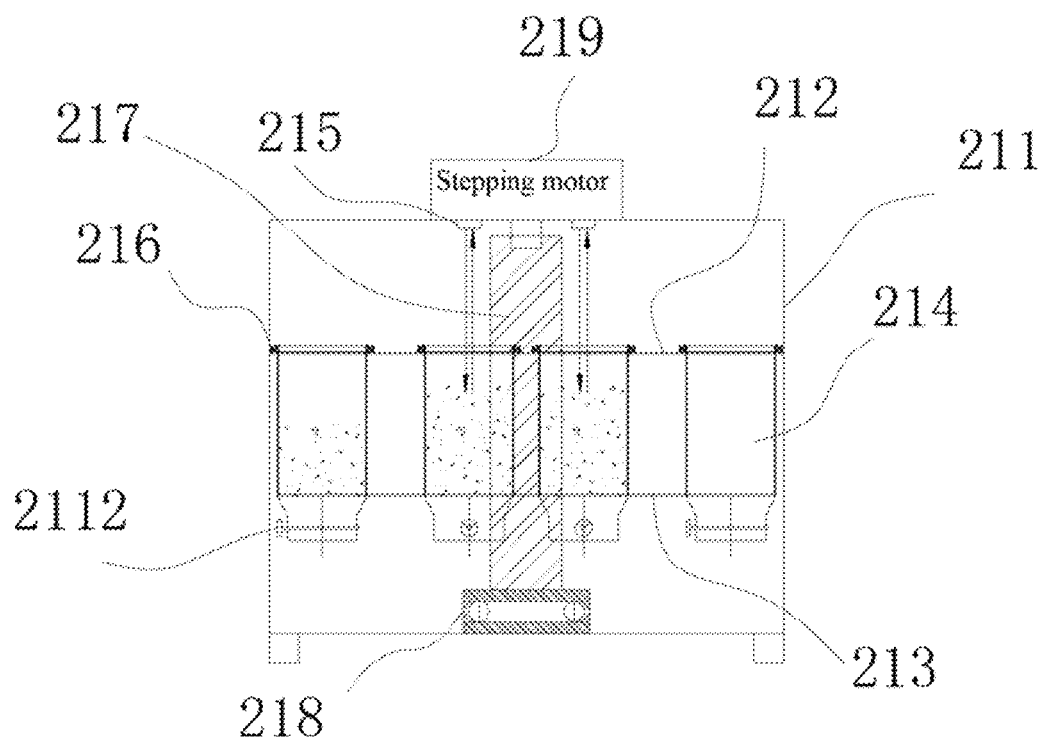
FIG. 3 is a front view of a coal and gangue identification device provided by embodiment 2.

Referring to FIG. 2 and FIG. 3, the present embodiment provides one structure of the coal and gangue identification device in embodiment 1.

In the present embodiment, the rotary supporting frame includes a first rotating shaft 217 that is vertically disposed, and a loading bracket that is connected with the first rotating shaft 217 and synchronously rotates with the first rotating shaft 217. Specifically, in the present embodiment, the first rotating shaft 217 is connected with a first motor 219 used to drive the first rotating shaft to rotate. The bottom end of the first rotating shaft 217 is also provided with an axial thrust bearing 218 to ensure steady rotation. In the present embodiment, the base 1 is also provided with a first barrel body 211, and the top of the first barrel body 211 is opened. The first rotating shaft 217 is arranged in the first barrel body 211 through the axial thrust bearing 218, and all the loading units are also located in the first barrel body 211. As such, when the distribution queuing device 100 injects the mineral aggregate to the loading unit of the material adding region 20b, the mineral aggregate that does not fall into the first weighing barrel 214 can be collected by means of the first barrel body 211 to avoid scattering and falling of the mineral aggregate. In the present embodiment, the first motor 219 is connected with the first barrel body 211 through a structure such as a connection rod, and is located at the top of the first rotating shaft 217. The loading unit is composed of one or more first weighing barrels 214 arranged on the loading bracket. Specifically, as shown in the figures, in the present embodiment, each loading unit includes two first weighing barrels 214 disposed side by side.

Figure 4:
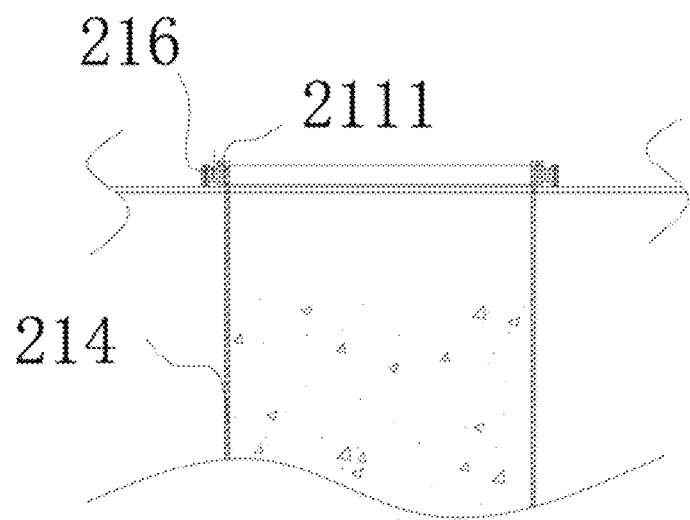
FIG. 4 is a structural installation diagram of a first weighing barrel used in embodiment 2.

Referring to FIG. 4, in the present embodiment, the bottom of each first weighing barrel 214 is provided with a first discharge electromagnetic valve 2112. When the loading unit rotates with the first rotating shaft 217 to the unloading region 20d, the first discharge electromagnetic valves 2112 on the corresponding first weighing barrels 214 are opened to facilitate unloading. In the present embodiment, the first discharge electromagnetic valve 2112 is arranged at the bottom of the first weighing barrel 214, and the lower end of the first weighing barrel 214 is provided with a conical outlet to ensure that the first weighing barrel 214 is fully unloaded when the first discharge electromagnetic valve 2112 is opened.

In the present embodiment, the loading bracket includes an upper supporting disk 212 and a lower supporting disk 213. The upper supporting disk 212 and the lower supporting disk 213 are both horizontally sleeved on the first rotating shaft 217. Specifically, in the present embodiment, the upper supporting disk 212 and the lower supporting disk 213 are both ring-like plates, and are concentric with the first rotating shaft 217. Furthermore, the upper supporting disk 212 and the first rotating shaft 217, and the lower supporting disk 213 and the first rotating shaft 217 are connected through supporting connection rods 2110. The supporting connection rods 2110 extend in a radial direction of the first rotating shaft 217.

The upper supporting disk 212 and the lower supporting disk 213 are provided with through holes corresponding to every first weighing barrel 214, and the through holes correspond to each other in a vertical direction and are used to fix the first weighing barrel 214. Furthermore, the diameter of the through hole formed in the lower supporting disk 213 is slightly greater than the diameter of the weighing barrel to prevent an interaction force between the lower supporting disk 213 and the first weighing barrel 214 from affecting the weighing accuracy and also prevent deflection of the weighing barrel. Specifically, in the present embodiment, the upper end of the first weighing barrel 214 is provided with a ring-like overlap edge 2111 extending to the outside. The arrangement of the ring-like overlap edge 2111 can prevent the first weighing barrel 214 from falling off to reinforce supporting and limiting from the upper supporting disk 212 to the first weighing barrel 214.

Figure 5:
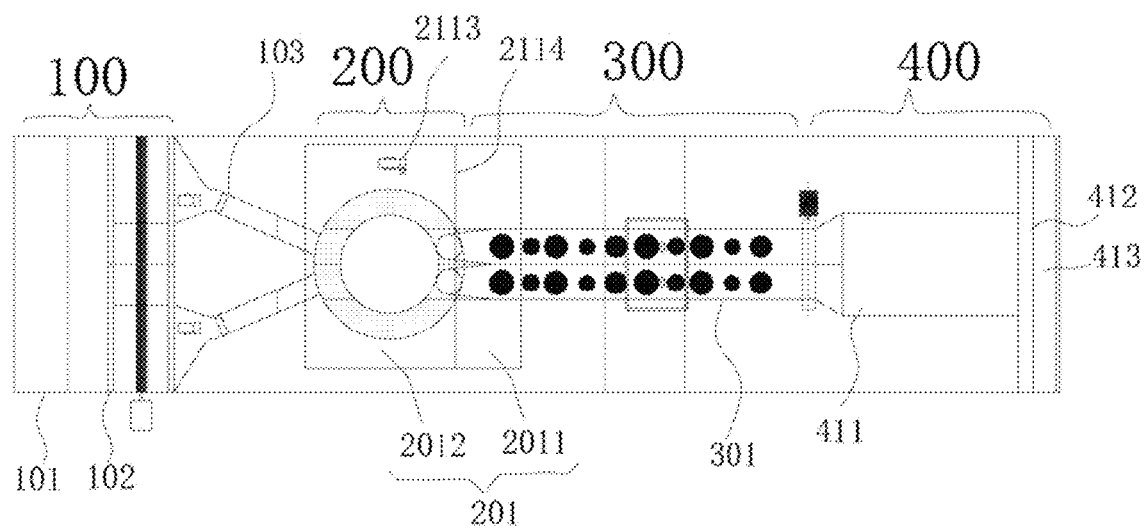
FIG. 5 is a top view of a first high-accuracy coal and gangue identification system provided by the present invention.

Referring to FIG. 5, on the basis of the present embodiment, in embodiment 1, the weighing unit includes a plurality of first weighing sensors 216; the plurality of first weighing sensors 216 respectively correspond to the first weighing barrels 214; the first weighing sensors 216 are all arranged on the upper supporting disk 212 and are located at the peripheries of the corresponding first weighing barrels 214; and the overlap edges of the first weighing barrels 214 are abutted against the corresponding first weighing sensors 216. In specific implementation, the first weighing sensor 216 uses a ring-like axial weighing sensor, and is sleeved at the periphery of the corresponding first weighing barrel 214. The liquid level detection device includes two first liquid level sensors 215; and the two first liquid level sensors 215 are both arranged at the top of the first barrel body 211 and respectively correspond to the water injection region 20a and the volume measurement region 20c to respectively detect a volume of the clear water in the first weighing barrel 214 after water injection in the water injection region 20a and a mixed volume of the mineral aggregate and water in the volume measurement region 20c.

On the basis of the present embodiment, in embodiment 1, the water injection unit includes a first metering pump 2113 and a sprayer that is arranged on the base 1 and is used to inject water to the first weighing barrel 214 of the water injection region 20a. The sprayer is communicated with the circulating water tank 201 by means of the first metering pump 2113 to realize quantitative water injection for the first weighing barrel 214.

On the basis of the present embodiment, in embodiment 1, a filtration division layer 2114 is arranged in the circulating water tank 201; the filtration division layer 2114 divides the circulating water tank 201 into a muddy water chamber 2011 and a clear water chamber 2012; the dewatering screen 202 is arranged above the muddy water chamber 2011; and the clear water chamber 2012 is used to supply water to the water injection unit. As such, muddy water separated by the dewatering screen 202 enters the muddy water chamber 2011; the water in the muddy water chamber 2011 is supplemented to the clear water chamber 2012 after being filtered via the filtration division layer, so that cyclic use of the clear water is guaranteed, and the risk of blockage of the water injection unit is avoided.

Embodiment 3: Rotating Wheel Type Coal and Gangue Identification Device

The present embodiment provides another structure of the coal and gangue identification device in embodiment 1.

Referring to FIG. 7 to FIG. 11, in the present embodiment, the rotary supporting frame includes a second rotating shaft 225. The second rotating shaft 225 is horizontally mounted on the base 1 and is connected with a second motor 229 used to drive the second rotating shaft to rotate. A second weighing barrel 227 serving as a loading unit is arranged on the second rotating shaft 225, and is uniformly distributed in a circumferential direction of rotation, and the second weighing barrel 227 synchronously rotates with the second rotating shaft 225. An opening direction of the second weighing barrel 227 is consistent with a rotation direction of the second rotating shaft 225, and the second weighing barrel 227 located in the water injection region 20a is located in the circulating water tank 201. As such, with the rotation of the second rotating shaft 225, when the second weighing barrel 227 enters the circulating water tank 201, and a motion trajectory of the second weighing barrel 227 submerges in water, the second weighing barrel 227 also undergoes water injection with the rotation of the second rotating shaft 225.

In the present embodiment, the water is always circulated between the circulating water tank 201 and the second weighing barrel 227, and the second weighing barrel 227 is uniformly distributed in the circumferential direction of the second rotating shaft 225, so that it can be ensured that the water injection volume of the second weighing barrel 227 is the same at each time to realize quantitative setting of the water injection volume of the second weighing barrel 227 by means of adjustment of the water level in the circulating water tank 201.

In the present embodiment, by means of setting the opening direction of the second weighing barrel 227, after the opening of the second weighing barrel 227 is higher than the water level in the circulating water tank 201, the volume of the second weighing barrel 227 is gradually increased on a motion trajectory with a certain length, i.e., the material adding region 20b. As such, by means of setting the rotation speed of the second rotating shaft 225 and a discharge time interval of the distribution queuing device 100 relative to the rotation speed of the second rotating shaft 225, it can be ensured that the second weighing barrel 227 enters the material adding region 20b and is then filled with the mineral aggregate by means of the distribution queuing device 100 to ensure that there is no water overflowing from the second weighing barrel 227 after the mineral aggregate fills.

Specifically, in embodiment 1, by means of setting the length of the discharge chute 103, the speed of the first conveying belt, and a feeding time interval of the star-type feeder 102, the filling time of the second weighing barrel 227 can be controlled. i.e., the position of the second weighing barrel 227 on the motion trajectory at the beginning of filling. Specifically, in the present embodiment, the opening direction of the second weighing barrel 227 is a tangent direction of rotation trajectory circle.

In the present embodiment, the second rotating shaft 225 is sleeved with a rotatably symmetric supporting part 226 that is of a quadrilateral star column structure, and each outer edge of the supporting part 226 is provided with one outer side plate. A slope of the supporting part 226 located between the outer edge and an inner edge is recorded as an edge slope; the edge slope opposite to the position of the outer side plate is recorded as an opposite slope; the edge slope located between the outer side plate and the corresponding opposite slope is recorded as a connection bottom surface; two opposite ends of the outer side plate are respectively provided with a first connection side plate and a second connection side plate; the outer side plate cooperates with the corresponding opposite slope, the connection bottom surface, a first connection side plate, and a second connection side plate to form the second weighing barrel 227. In the present embodiment, the outer side plate is parallel to the corresponding opposite slope.

Figure 7:
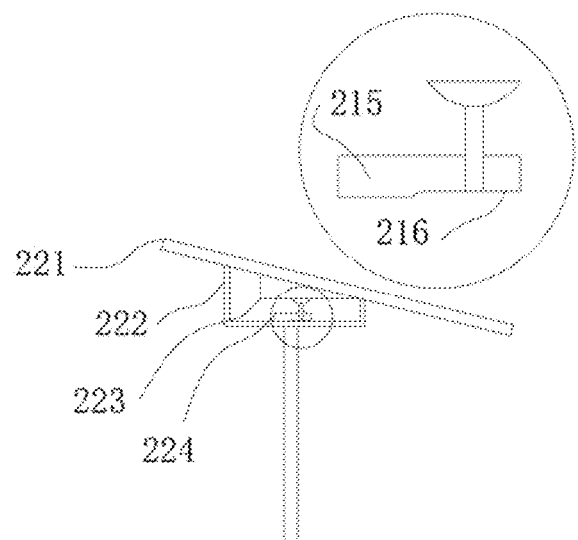
FIG. 7 is a structural diagram of a weighing unit in embodiment 3.
Figure 8:
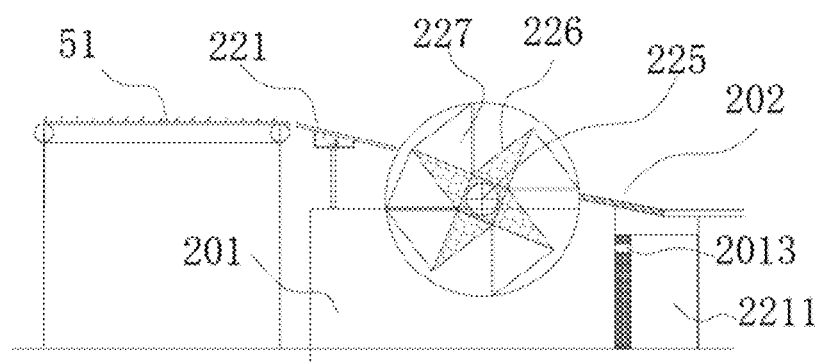
FIG. 8 is a structural diagram of a rotating wheel type coal gangue identification device provided by embodiment 3 in a water injection state.
Figure 9:
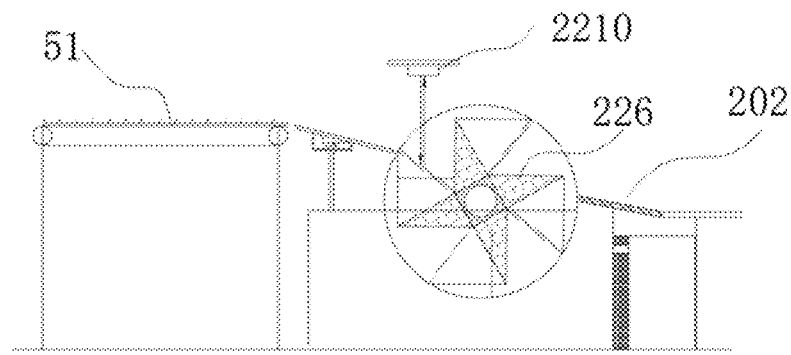
FIG. 9 is a structural diagram of a rotating wheel type coal gangue identification device provided by embodiment 3 in a liquid level measurement state.
Figure 10:
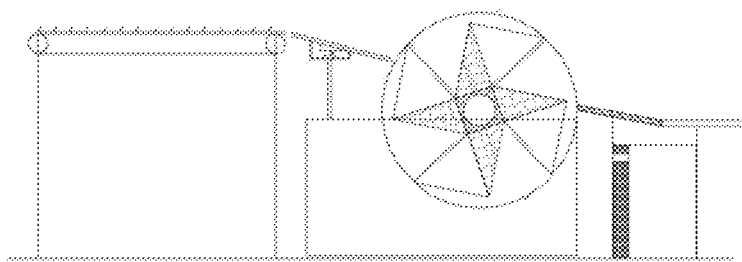
FIG. 10 is a structural diagram of a rotating wheel type coal gangue identification device provided by embodiment 3 in an unloading.

Referring to FIG. 7, in the present embodiment, the weighing unit includes a balance plate 221, a balance box 222, and a second weighing sensor 224. The balance box is arranged on the base 1; and the balance plate 221 is arranged on the balance box and is located between the distribution queuing device 100 and the second rotating shaft 225. The balance plate 221 is inclined, with a high end facing the distribution queuing device 100 and a bottom end facing the second rotating shaft 225 and corresponding to the opening of the second weighing barrel 227 located in the material adding region 20b. The mineral aggregate output by the distribution queuing device 100 slides through the balance plate 221 into the second weighing barrel 227 located in the material adding region 20b. The second weighing sensor 224 is arranged in the balance box, and is used to weigh the balance plate 221 to count the weight of the mineral aggregate passing through the balance plate 221. Specifically, the second weighing sensor 224 can be arranged at the bottom of the balance plate 221, and the bottom of the balance plate 221 is provided with one straight rod abutting against the second weighing sensor 224, so that the balance plate 221 applies a force to the second sensor.

In specific implementation, soft connection, such as an elastic pad, is arranged between the balance plate 221 and the balance box 222 to guarantee the measurement accuracy of the second weighing sensor 224. The lower surface of the balance plate 221 can also be provided with a triangular fixture 223. The triangular fixture 223 is of a right-angle structure, with a slope attached to the balance plate 221, and a surface of the triangular fixture on a horizontal plane is directly or indirectly abutted against the second weighing sensor 224 to guarantee accurate measurement of a load on the balance plate 221.

Specifically, in the present embodiment, the second weighing sensor 224 uses a cantilever weighing sensor, a cantilever of which abuts against the triangular fixture 223 from the bottom.

Figure 11:
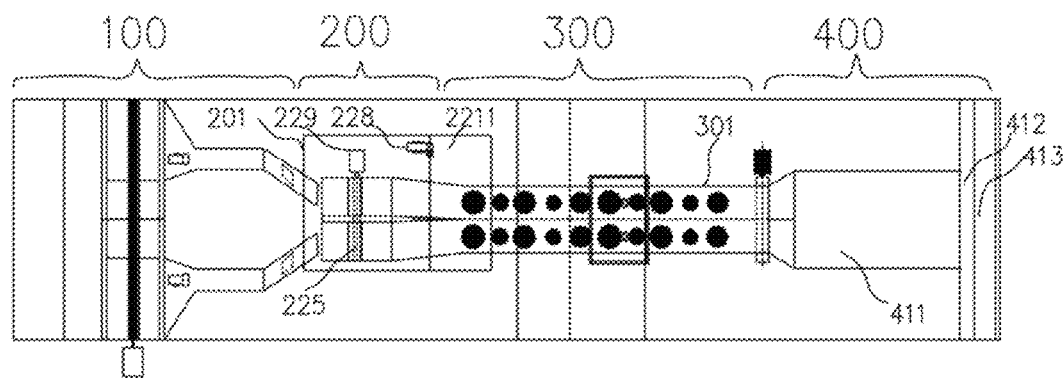
FIG. 11 is a top view of a second high-accuracy coal and gangue identification system provided by the present invention.

Referring to FIG. 11, on the basis of the present embodiment, in embodiment 1, the processor calculates, according to a detected value of the second weighing sensor 224, the weight of the mineral aggregate that passes through the balance plate 221 and enters the second weighting barrel 227.

In the rotating wheel type coal and gangue identification device of the present embodiment, a water supplementing tank 2211 and an overflow slot 2013 are further provided. The circulating water tank 201 is provided with an overflow port; the overflow slot 2013 is connected between the circulating water tank 201 and the water supplementing tank 2211 to convey water that overflows out of the circulating water tank 201 from the overflow port to the water supplementing tank 2211 for storage. Specifically, a second metering pump 228 used to convey the water in the water supplementing tank 2211 back to the circulating water tank 201 is also arranged between the water supplementing tank 2211 and the circulating water tank 201 to realize cyclic use of water resources.

On the basis of the present embodiment, in embodiment 1, the liquid level detection device uses a second liquid level sensor 2210 mounted on the base 1 by means of a supporting structure, and is used to detect a liquid level in the second weighing barrel 227 when the outer side plate is vertical, so as to facilitate calculation.

Embodiment 4: Coal and Gangue Sorting System

The system in the present embodiment includes a coal and gangue identification device and the coal and gangue sorting device. The coal and gangue identification device can specifically use the coal and gangue identification device provided by embodiment 2 or embodiment 3, or can use a γ-ray type coal and gangue identification device. The coal and gangue sorting device is used to respectively transport coal and gangue that are identified by the coal and gangue identification device 200 to specified positions.

In specific implementation, the system in the present embodiment can also include a distribution queuing device, i.e., a coal and gangue sorting device is added on the basis of embodiment 1 to obtain the system in the present embodiment.

Embodiment 5: Coal and Gangue Sorting Device

Figure 12:
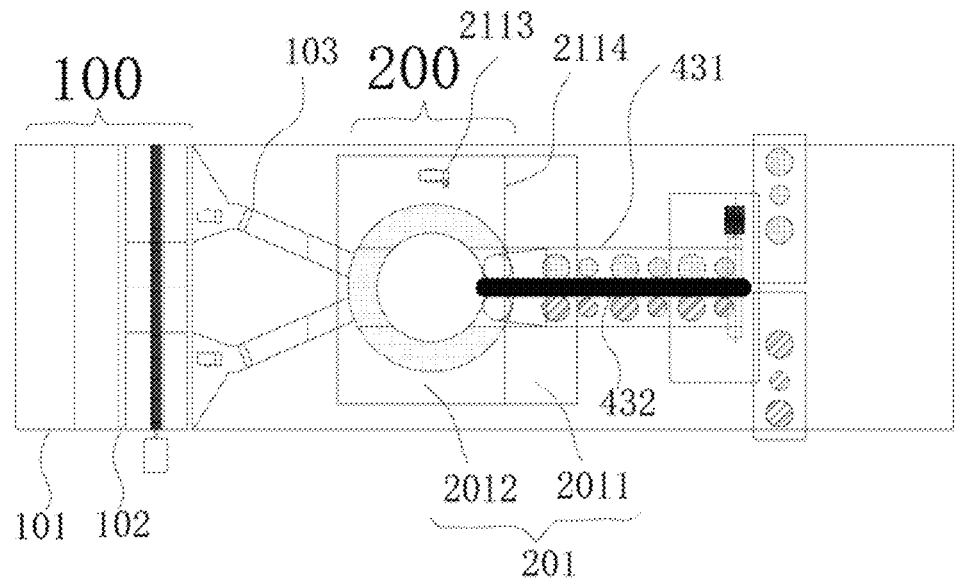
FIG. 12 is a top view of a third high-accuracy coal and gangue identification system provided by the present invention.
Figure 13:
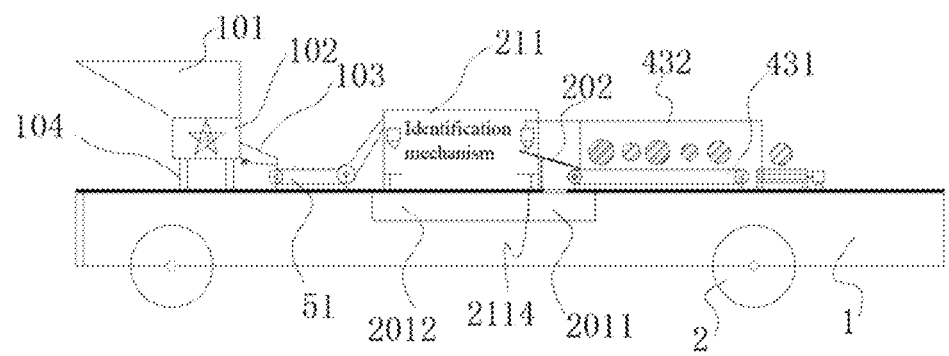
FIG. 13 is a front view of the system shown in FIG. 12.

Referring to FIG. 12 and FIG. 13, the present embodiment provides one specific structure of the coal and gangue sorting device in embodiment 4. The coal and gangue sorting device includes a second conveying belt 431 mounted on the base 1. A gangue runner and a clean coal runner are disposed on the second conveying belt 431 side by side.

Specifically, a mineral aggregate is discharged to the clean coal runner of the second conveying belt 431 when the coal and gangue identification device identifies that the mineral aggregate is clean coal; and the mineral aggregate is discharged to the gangue runner of the second conveying belt 431 when the coal and gangue identification device identifies that the mineral aggregate is gangue. With the motion of the second conveying belt 431, the clean coal on the clean coal runner and the gangue on the gangue runner are respectively conveyed to the specified positions.

In the present embodiment, the second conveying belt 431 is provided with a runner partition plate 432 in the motion direction to realize separation of the gangue runner from the clean coal runner.

Specifically, when embodiment 1 uses the coal and gangue identification device shown in embodiment 2, a middle partition plate can further be arranged on the dewatering screen 202 to partition the dewatering screen 202 into both sides that respectively correspond to the clean coal runner and the gangue runner. If the processor identifies that the mineral aggregate in the first weighing barrel 214 is clean coal, when the first weighing barrel 214 moves to the side of the dewatering screen 202 corresponding to the clean coal runner, the first discharge electromagnetic valve 2112 is opened for blanking; and if the processor identifies that the mineral aggregate in the first weighing barrel 214 is gangue, when the first weighing barrel 214 moves to the side of the dewatering screen 202 corresponding to the gangue runner, the first discharge electromagnetic valve 2112 is opened for blanking.

Specifically, when embodiment 1 uses the coal and gangue identification device shown in embodiment 3, a transition mechanism can further be disposed between the dewatering screen 202 and the second conveying belt 431. Specifically, the transition mechanism can be configured to be a mechanical arm controlled by the processor of the coal and gangue identification device, so that the processor controls the mechanical arm to move, according to a mineral aggregate identification result, the mineral aggregate to the corresponding clean coal runner or gangue runner after the mineral aggregate is dewatered via the dewatering screen 202. The transition mechanism can also be configured to be a sliding rail located between the dewatering screen 202 and the second conveying belt 431; the high end of the sliding rail is rotatably mounted and faces the dewatering screen 202, and the low end of the sliding rail is slidably mounted and faces the conveying belt; and both ends of a motion trajectory of the low end of the sliding rail respectively correspond to the gangue runner and the clean coal runner. When the low end of the sliding rail slides to one side of the gangue runner, the mineral aggregate on the dewatering screen 202 enters the gangue runner via the sliding rail; and when the low end of the sliding rail slides to one side of the clean coal runner, the mineral aggregate on the dewatering screen 202 enters the clean coal runner via the sliding rail. In specific implementation, the processor in the coal and gangue identification device can control a sliding rail driving motor to adjust the position of the low end of the sliding rail, thereby realizing adjustment of the position of the sliding rail according to the mineral aggregation identification result to perform directed conveying of the mineral aggregate.

Embodiment 6: Coal and Gangue Separation Device

Referring to FIG. 14 to FIG. 20, the coal and gangue separation device provided by the present embodiment includes a first supporting seat 414, a cantilever shaft 415, a guide part 411, and a plurality of stock bins.

The cantilever shaft 415 is horizontally mounted on the first supporting seat 414; a fixed end of the guide part 411 is connected with the cantilever shaft 415, and the guide part 411 rotates around the cantilever shaft 415; and inlets of the plurality of stock bins are sequentially distributed on a rotation trajectory of a movable end of the guide part 411. As such, the guide part 411 can be enabled to correspond to different inlets of the stock bins by means of adjusting an inclination angle of the guide part 411, so that the mineral aggregate enters the corresponding stock bin by means of the guide part 411. Specifically, in the present embodiment, the guide part 411 is in an inclined state when corresponding to the inlet of any stock bin, so that the mineral aggregate on the guide part 411 slides into the corresponding stock bin under the gravity.

Specifically, in the present embodiment, the guide part 411 is composed of a plurality of cantilever grate bars 4110 that are rotatably mounted on the cantilever shaft 415 and parallel to each other. As such, when a mineral aggregate appears on the guide part 411, the corresponding cantilever grate bar 4110 is adjusted to rotate to adapt to the position and the width of the mineral aggregate to convey the mineral aggregate to a slideway of the corresponding stock bin, thereby avoiding redundant energy caused by overall rotation of the guide part 411; meanwhile, adjusting the cantilever grate bars 4110 by means of the corresponding mineral aggregates is also favorable for forming a plurality of passages corresponding to the inlets of different stock bins according to the needs of the mineral aggregates, thereby improving the mineral aggregate collection efficiency.

Specifically, in the present embodiment, each cantilever grate bar 4110 is provided with a corresponding grate bar driving mechanism.

Figure 14:
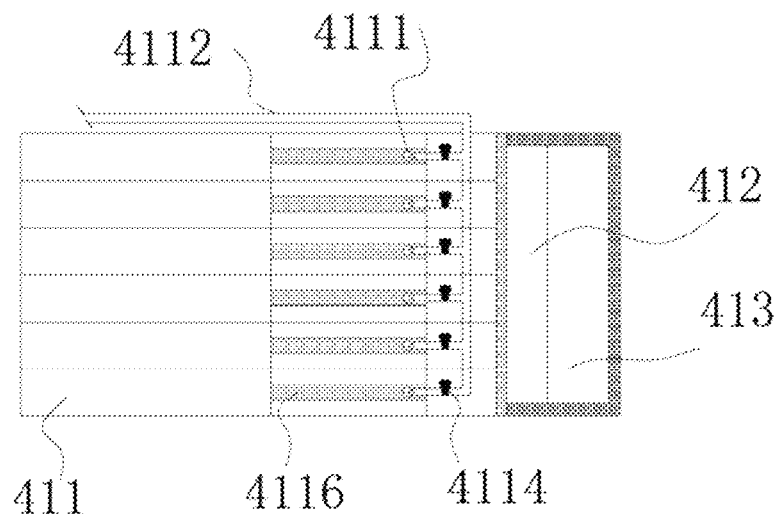
FIG. 14 is a top view of a coal and gangue separation device having a first grate bar driving mechanism provided by embodiment 6.
Figure 15:
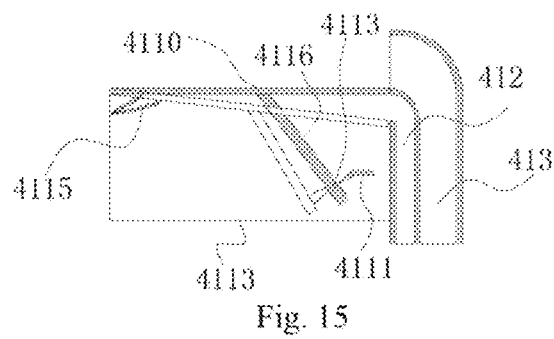
FIG. 15 is a front view of a coal and gangue separation device having a first grate bar driving mechanism provided by embodiment 6.

Referring to FIG. 14 and FIG. 15, in the present embodiment, a first grate bar driving mechanism is provided, including a first reset spring 4115, a first push rod 4116, and a first high-pressure nozzle 4111. The first reset spring 4115 is arranged below the corresponding cantilever grate bar 4110, with both ends respectively connected to the first supporting seat 414 and the corresponding cantilever grate bar 4110. In a natural state of the first reset spring 4115, the movable end of the corresponding cantilever grate bar 4110 corresponds to the stock bin having the inlet located at the highest position. The first high-pressure nozzle 4111 is arranged on the first supporting seat 414 and blows air to the first push rod 4116 to push the first push rod 4116 by means of air pressure to drive the cantilever grate bar 4110 to rotate downwards, so as to adjust a position correspondence relation between the movable end of the cantilever grate bar 4110 and the stock bin to realize feeding to different stock bins. Specifically, the grate bar driving mechanism further includes a first groove 4113 formed in a side of the first push rod 4116 facing the first high-pressure nozzle 4111, and the first high-pressure nozzle 4111 blows air to the first groove 4113. In the present embodiment, each first high-pressure nozzle 4111 is connected with an external air supply device by means of one first air feed electromagnetic valve 4114. Specifically, in this implementation mode, the external air supply device is connected with all the first air feed electromagnetic valves 4114 by means of a first air feed pipe 4112 to feed air.

Figure 16:
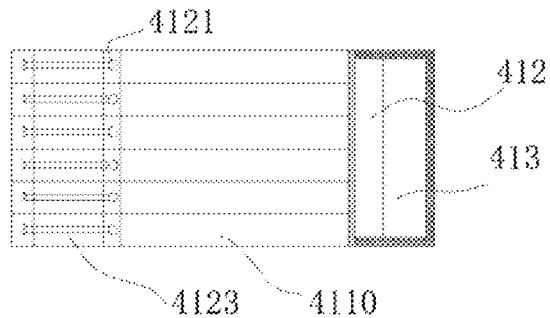
FIG. 16 is a top view of a coal and gangue separation device having a second grate bar driving mechanism provided by embodiment 6.
Figure 17:
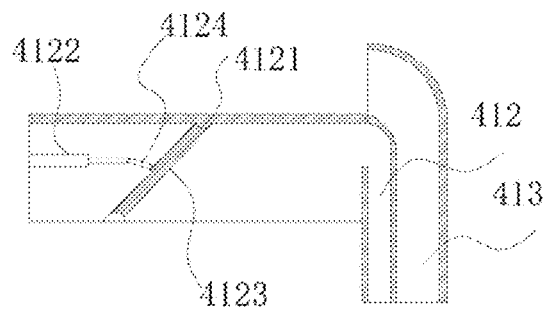
FIG. 17 is a front view of the device shown in FIG. 16 under a first implementation mode.
Figure 18:
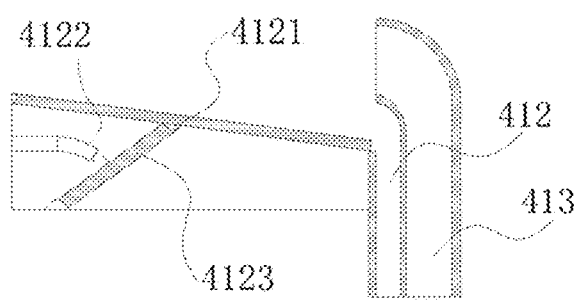
FIG. 18 is a front view of the device shown in FIG. 16 under a second implementation mode.

Referring to FIG. 16, FIG. 17, and FIG. 18, in the present embodiment, a second grate bar driving mechanism provided includes a second push rod 4122, a first extrusion rod 4123, and a first sliding chute that is arranged on the lower surface of the cantilever grate bar 4110 and located on a rotatable plane of the cantilever grate bar 4110. The lower end of the first extrusion rod 4123 is hinged with the first supporting seat 414; and the rotatable plane of the first extrusion rod 4123 overlaps the rotatable plane of the cantilever grate bar 4110. The upper end of the first extrusion rod 4123 is provided with a first pulley 4121, and the first pulley 4121 is embedded into the first sliding chute. In the present embodiment, the second push rod 4122 is an electric telescopic rod or a pneumatic telescopic rod; the second push rod 4122 is arranged on the first supporting seat 414; a free end of the second push rod 4122 is provided with a first hinging connection rod 4124; one end of the first hinging connection rod 4124 is hinged with the first extrusion rod 4123; and the other end of the first hinging connection rod 4124 is hinged with the free end of the second push rod 4122, so as to drive the first extrusion rod 4123 to rotate by means of extension and retraction of the second push rod 4122 to adjust the inclination angle of the cantilever grate bar 4110. Referring to FIG. 18, in specific implementation, the second push rod 4122 can also be configured to be an arc-shaped pneumatic; one end of the second push rod 4122 is fixedly connected with the first extrusion rod 4123, and the other end of the second push rod is fixedly connected with the first supporting seat 414; the second push rod 4122 is located on a concentric circle of the rotation trajectory circle of the first extrusion rod 4123; and the deformation of the second push rod 4122 is controlled to drive the second extrusion rod 4133 to rotate to adjust the inclination angle of the cantilever grate bar 4110.

Figure 19:
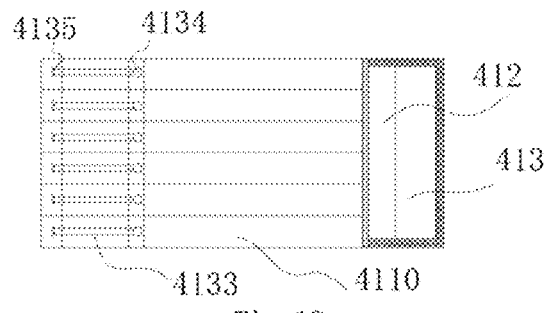
FIG. 19 is a top view of a coal and gangue separation device having a third grate bar driving mechanism provided by embodiment 6.
Figure 20:
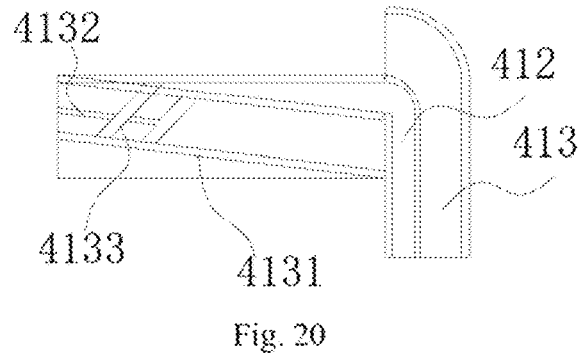
FIG. 20 is a front view of a coal and gangue separation device having a third grate bar driving mechanism provided by embodiment 6.

Referring to FIG. 19 and FIG. 20, in the present embodiment, a third grate bar driving mechanism provided includes a fixed rod 4131, a third push rod 4132, a second extrusion rod 4133, and a second sliding chute arranged on the lower surface of the cantilever grate bar 4110. The fixed rod 4131 is slantways arranged on the first supporting seat 414, and the fixed rod 4131 is provided with a third sliding chute; and the third sliding chute and the second sliding chute are located in the same plane. Both ends of the second extrusion rod 4133 are respectively provided with a second pulley 4134 and a third pulley 4135; and the second pulley 4134 and the third pulley 4135 are respectively embedded into the second sliding chute and the third sliding chute. The third push rod 4132 uses a pneumatic telescopic rod or an electric telescopic rod; the third push rod 4132 is arranged on the first supporting seat 414; an extension and retraction direction of the third push rod 4132 is parallel to a lengthwise direction of the third sliding chute; and a movable end of the third push rod 4132 is connected with the second extrusion rod 4133. As such, extension and retraction of the third push rod 4132 can drive the second extrusion rod 4133 to slide along the third sliding chute to adjust the inclination angle of the cantilever grate bar 4110.

In the present embodiment, a fourth grate bar driving mechanism provided includes a fourth push rod. The fourth push rod uses a pneumatic telescopic rod or an electric telescopic rod; the fourth push rod is perpendicularly arranged on the first supporting seat 414; and the top end of the fourth push rod is in hinging connection with the lower surface of the cantilever grate bar 4110. As such, extension and retraction of the fourth push rod can drive the cantilever grate bar 4110 to rotate.

In the present embodiment, one surface plate can be directly configured as the guide part 411. At this time, the inclination angle of the guide part 411 can be manually adjusted. Any one of the above-mentioned grate bar driving mechanisms can also be applied to the guide part 411 to drive the guide part to rotate, thereby adjusting the guide part 411 to correspond to the inlets of the stock bins.

When the coal and gangue separation device provided by the present embodiment is used as a coal and gangue sorting device in embodiment 4, two stock bins are respectively used as a clean coal collection bin 413 and a gangue collection bin 412. As such, in the present embodiment, the inclination angle of the guide part/cantilever grate bar can be adjusted according to an identification result of the coal and gangue identification device on the mineral aggregate to ensure that clean coal enters the clean coal collection bin 413 by means of the guide part/cantilever grate bar and gangue enters the gangue collection bin 412 by means of the guide part/cantilever grate bar.

When the coal and gangue separation device provided by the present embodiment is used as the coal and gangue sorting device in embodiment 4, the first supporting seat 414 is mounted on the base 1 to ensure a stable position between the coal and gangue identification device and the coal and gangue separation device. In specific implementation, the first supporting seat 414 and the base 1 can also be integrated.

Embodiment 7: Coal and Gangue Separation System

Figure 6:
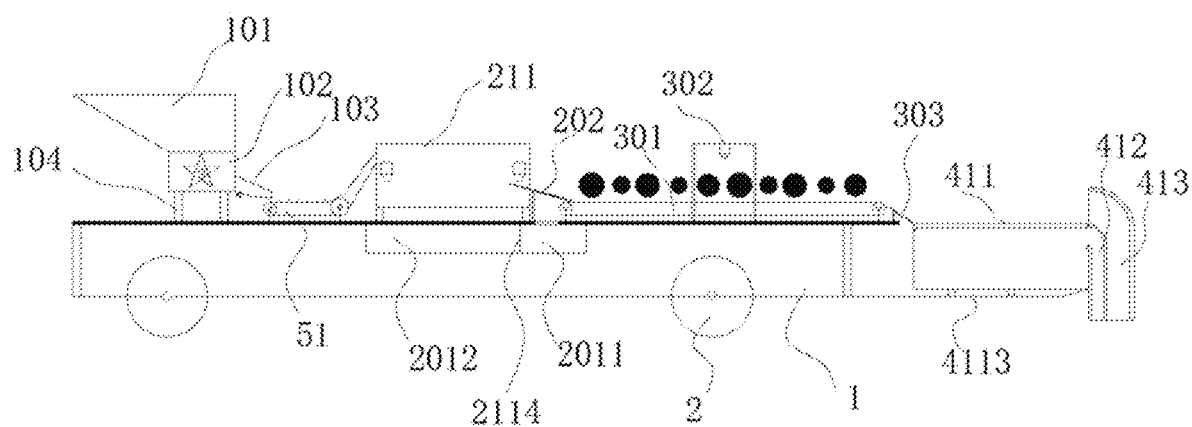
FIG. 6 is a front view of the system shown in FIG. 5.

Referring to FIG. 5, FIG. 6, and FIG. 11, on the basis of embodiment 4, a raw coal gangue-discharge complete system provided by the present embodiment uses the coal and gangue separation device disclosed in embodiment 6 as the coal and gangue sorting device, and a third conveying belt 301 is arranged between the coal and gangue identification device 200 and the coal and gangue separation device 400; the third conveying belt 301 is arranged on the base 1 and is used to transport the mineral aggregate dewatered by the dewatering screen 202 to the guide part 411. Specifically, in the present embodiment, the first supporting seat 414 and the base 1 are integrated.

As such, when the raw coal gangue-discharge system in the present embodiment works, the mineral aggregate in the receiving hopper 101 is input to the coal and gangue identification device via the distribution queuing device 100, and the coal and gangue identification device calculates a coal-to-gangue content ratio in the mineral aggregate; then, the coal and gangue identification device discharges the identified mineral aggregate to the dewatering screen 202; the mineral aggregate slides to the third conveying belt 301 along the dewatering screen 202; and the third conveying belt 301 carrying the mineral aggregate moves to the coal and gangue separation device to transport the mineral aggregate to the guide part 411.

The raw coal gangue-discharge system in the present embodiment further includes a coal and gangue tracking unit 300. The coal and gangue tracking unit 300 is used to identify the mineral aggregate on the third conveying belt 301 and track and locate the mineral aggregate. Specifically, in the present embodiment, the coal and gangue identification device 200 identifies coal and gangue; the coal and gangue tracking unit 300 acquires an identification result of the coal and gangue identification device 200, and performs image recording and tracking on the identified clean coal and gangue to accurately identify constituents and a position of each mineral aggregate on the third conveying belt 301, so that when the mineral aggregate enters the guide part 411, the rotation angle of the corresponding cantilever grate bar 4110 is accurately adjusted. Therefore, the mineral aggregate enters the clean coal collection bin 413 when the mineral aggregate is clean coal and enters the gangue collection bin 412 when the mineral aggregate is gangue.

Specifically, in the present embodiment, the coal and gangue tracking unit 300 includes a camera 302 and an image processing module. The camera 302 is used to collect an image of the mineral aggregate on the third conveying belt 301; and the image processing module is used to identify the image collected by the camera 302 and judge whether the mineral aggregate in the image is clean coal or gangue. Specially, in the present embodiment, the coal and gangue tracking unit 300 firstly obtains the identification result of the coal and gangue identification device 200 on the mineral aggregate; the coal and gangue tracking unit 300 collects the identified mineral aggregate image as a reference sample, and each reference sample is associated with an identification result; and then the coal and gangue tracking unit 300 compares the collected image of the mineral aggregate on the third conveying belt 301 with the reference sample to track and accurately locate the mineral aggregate on the third conveying belt 301, so that the coal and gangue separation device accurately feeds each mineral aggregate to the corresponding stock bin according to the constituents in combination with the position of the mineral aggregate. Specifically, in the present embodiment, when the mineral aggregate enters the corresponding stock bin, the coal and gangue tracking unit 300 deletes the reference sample corresponding to the mineral aggregate to improve the comparison efficiency between the mineral aggregate image and the reference sample, thereby guaranteeing the timeliness and the accuracy of tracking and localization for the mineral aggregate.

In specific implementation, the coal and gangue identification device 200 in the present embodiment can further use a 7 ray identification device. Moreover, along the motion direction of the third conveying belt 301, the γ ray identification device is used to identify the mineral aggregate located at the front end of the coal and gangue tracking unit 300.

In specific implementation, a transfer chute 303 can also be arranged between the third conveying belt 301 and the guide part 411; the transfer chute 303 is slantways arranged on the first supporting seat 414; the high end of the transfer chute 303 faces the third conveying belt 301, and the low end of the transfer chute 303 faces the guide part 411, so that the mineral aggregate slides onto the guide part 411 by means of the transfer chute 303 after being separated from the third conveying belt 301 to ensure steady transportation of the mineral aggregate.

Figure 21:
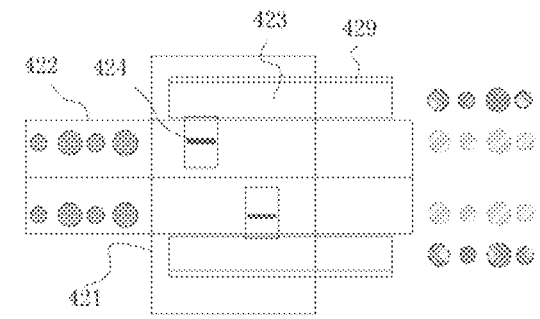
FIG. 21 is a top view of a coal and gangue sorting device in Embodiment 8.
Figure 22:
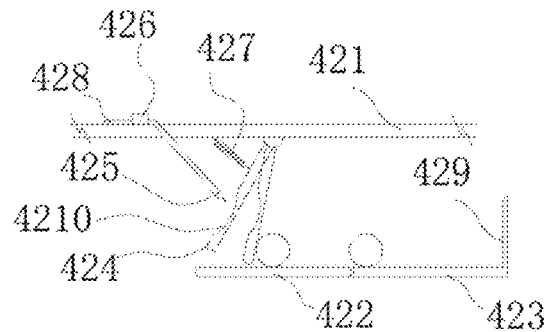
FIG. 22 is a front view of the coal and gangue sorting device shown in FIG. 21.
Figure 23:
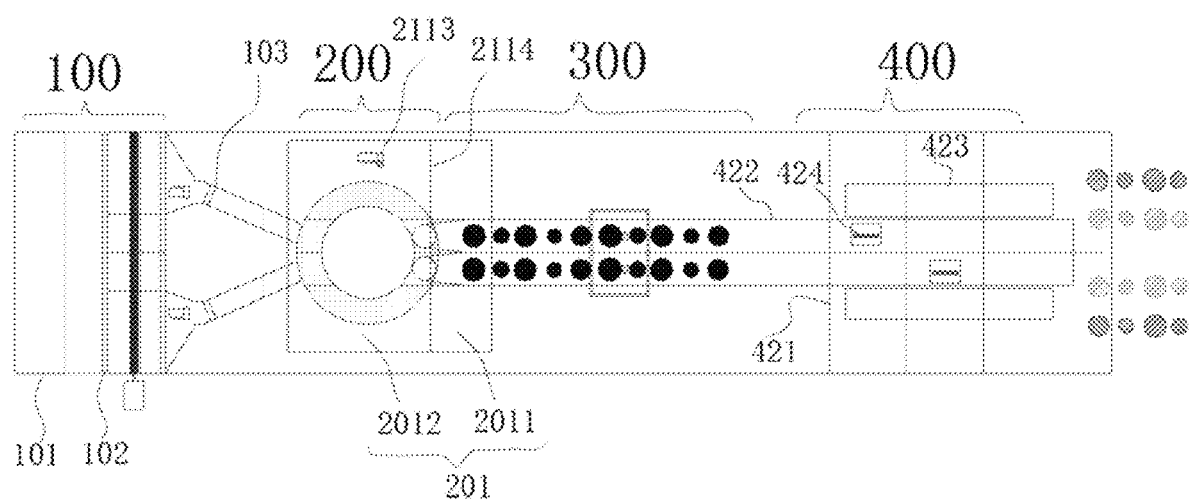
FIG. 23 is a top view of the high-accuracy coal and gangue identification system in embodiment 8.
Figure 24:
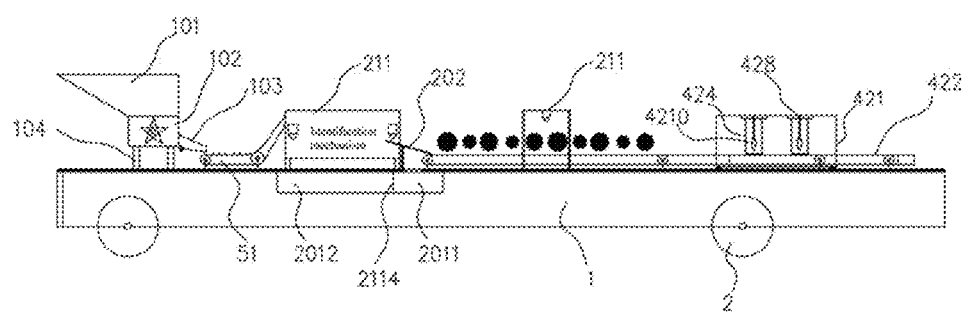
FIG. 24 is a top view of the high-accuracy coal and gangue identification system in FIG. 23.

Embodiment 8: Coal and Gangue Sorting Device and Raw Coal Gangue-Discharge System Referring to FIG. 21 and FIG. 22, the coal and gangue sorting device provided by the present embodiment includes a second supporting seat, a separation bracket 421, a fourth conveying belt 422, a fifth conveying belt 423, and a deflector rod 424.

The fourth conveying belt 422 and the fifth conveying belt 423 are disposed on the second supporting seat side by side; the separation bracket 421 is arranged on the second supporting seat; the deflector rod 424 is rotatably mounted on the separation bracket 421 and is located above the fourth conveying belt 422; a rotation direction of the deflector rod 424 is perpendicular to a motion direction of the fourth conveying belt 422; and the deflector rod 424 is used to push the mineral aggregate on the fourth conveying belt 422 onto the fifth conveying belt 423.

As such, separation of the mineral aggregation from the fourth conveying belt 422 can be realized by means of pushing of the deflector rod 424, so that different mineral aggregates are respectively conveyed to different directions by means of the fourth conveying belt 422 and the fifth conveying belt 423. In the present embodiment, two opposite sides of the fourth conveying belt 422 are each provided with one fifth conveying belt 423, so that the fifth conveying belts 423 conveniently convey the mineral aggregate pushed out of the fourth conveying belt 422 by the deflector rod 424 in any direction.

In the present embodiment, a plurality of deflector rods 424 are provided, and the plurality of deflector rods 424 are distributed in the motion direction of the fourth conveying belt 422. As such, by means of the pushing from the plurality of deflector rods 424, if there are too many mineral aggregates on the fourth conveying belt 422, continuous short-distance pushing by the plurality of deflector rods 424 guarantees accurate separation of the mineral aggregates. In the same way, the plurality of deflector rods 424 are also sequentially distributed in a width direction of the fourth conveying belt 422.

In the present embodiment, each fifth conveying belt 423 is provided with one corresponding baffle plate 429. The baffle plate 429 is arranged on the second supporting seat and is located on a side of the corresponding fifth conveying belt 423 facing away from the fourth conveying belt 422. The baffle plate 429 is used to prevent the mineral aggregate pushed by the deflector rod 424 onto the fifth conveying belt 423 from falling off from the edge of the fifth conveying belt 423.

The coal and gangue sorting device in the present embodiment further includes a deflector rod driving mechanism. Each deflector rod 424 is provided with a corresponding deflector rod driving mechanism. The deflector rod driving mechanism includes a second reset spring 427, a second high-pressure nozzle 425, and a second air feed electromagnetic valve 426. Both ends of the second reset spring 427 are respectively connected with the separation bracket 421 and the corresponding deflector rods 424; the second high-pressure nozzle 425 is arranged on the separation bracket 421; and the second high-pressure nozzle 425 is used to spray air to the corresponding deflector rod 424 to drive the deflector rod 424 to rotate. The second high-pressure nozzle 425 is connected with the external air supply device by means of the corresponding second air feed electromagnetic valve 426. As such, the second air feed electromagnetic valve 426 is controlled to be opened to control the second high-pressure nozzle 425 to work to spray air to drive the deflector rod 424 to push the mineral aggregate on the fourth conveying belt 422. When the second air feed electromagnetic valve 426 is closed, the second high-pressure nozzle 425 stops working, and the deflector rod 424 is reset to the original position under the action of the reset elasticity of the second reset spring 427. Specifically, in the present embodiment, a side of the deflector rod 424 facing the second high-pressure nozzle 425 is provided with a second groove 4210, and the second high-pressure nozzle 425 sprays air to the second groove 4210.

Specifically, in the present embodiment, all the second high-pressure nozzles 425 share the same external air supply device. The external air supply device is connected to all the second high-pressure nozzles 425 by means of second air feed pipes 428. All the second air feed electromagnetic valves 426 are located between the corresponding second high-pressure nozzles 425 and the second air feed pipes 428.

When the coal and gangue sorting device provided by the present embodiment is used in embodiment 4 to form the raw coal gangue-discharge system, the second supporting seat is integrated with the base 1; the fourth conveying belt 422 is located on a side of the dewatering screen 202 away from the coal and gangue identification device, and the fourth conveying belt 422 is used to transport the mineral aggregate dewatered by the dewatering screen 202. In specific implementation, the fourth conveying belt 422 can be used as a clean coal conveying belt, and the fifth conveying belt 423 can be used as a gangue conveying belt; or, the fourth conveying belt 422 can be used as a gangue conveying belt, and the fifth conveying belt 423 can be used as a clean coal conveying belt. Meanwhile, a clean coal collection box and a gangue collection box can also be arranged on the base 1 to respectively correspond to the clean coal conveying belt and the gangue conveying belt.

In the present embodiment, control modules that are respectively connected with the coal and gangue identification device and all the second air feed electromagnetic valves 426 can be configured in combination with an automatic control technology. The control modules control, according to the identification result of the coal and gangue identification device on the mineral aggregate, the second air feed electromagnetic valves 426 corresponding to all the deflector rods 424 to work. That is, when the control module obtains the position of a certain mineral aggregate needing to be removed according to the coal and gangue identification device, the control module controls the second air feed electromagnetic valve 426 connected to the deflector rod 424 corresponding to the position of the mineral aggregate to be opened, so that the deflector rod 424 pushes the mineral aggregate onto the fifth conveying belt 423. Specifically, the control module controls the second air feed electromagnetic valve 426 to be closed after controlling the second air feed electromagnetic valve 426 to be opened for a period of time, thus facilitating resetting of the deflector rod 424.

In the present embodiment, a coal and gangue tracking unit 300 can also be arranged on the base 1. The coal and gangue tracking unit 300 is located between the dewatering screen 202 and the deflector rod 424 and is used to track and locate the mineral aggregate on the fourth conveying belt 422 according to the identification result of the coal and gangue identification device on the mineral aggregate. Meanwhile, the control modules are connected with the coal and gangue tracking unit 300, and control, according to the tracking and localization of the coal and gangue tracking unit 300 for the mineral aggregate, the second air feed electromagnetic valves 426 corresponding to all the deflector rods 424 to work.

Specifically, in the present embodiment, the coal and gangue tracking unit 300 includes a camera 302 and an image processing module. The camera 302 is used to collect an image of the mineral aggregate on the fourth conveying belt 422; and the image processing module is used to identify the image collected by the camera 302 and judge whether the mineral aggregate in the image is clean coal or gangue. Specifically, the working principle of the coal and gangue tracking unit 300 refers to embodiment 7.

In specific implementation, the coal and gangue tracking unit 300 in the present embodiment can also use a γ ray identification device.

In embodiment 1 to embodiment 8, in specific implementation, the dewatering screen 202 is composed of an upper guide plate, screen cloth and a lower guide plate. The upper guide plate, the screen cloth and the lower guide plate are disposed on the same inclined plane and are arranged from top to bottom. The upper guide plate is beneficial to the formation of an inertial motion of the mineral aggregate, so that the mineral aggregate passes through the screen cloth more steadily to reduce the friction influence. The installation position of the screen cloth corresponds to the circulating water tank 201 or the muddy water chamber 2011. The lower guide plate is used to abut with a mechanism at the rear end of the dewatering screen 202, such as the second conveying belt 431, the sliding rail or the third conveying belt or the fourth conveying belt 422, so that the mineral aggregate is conveyed to the rear-end mechanism via the lower guide plate after being dewatered by the screen cloth, which avoids run off of the clear water drained by the loading unit and also prevents the rear-end mechanism from being wetted and damaged.

In the above-mentioned embodiments, the base 1 is arranged to guarantee the stability of the relative positions between different devices to ensure connection of the working processes between different devices or units. In specific implementation, the base 1 can be removed, or the lower surface of the base 1 is further provided with wheels 2 to facilitate the movement of the base 1.

Embodiment 9: Linear Coal and Gangue Separation Device and System

Figure 25:
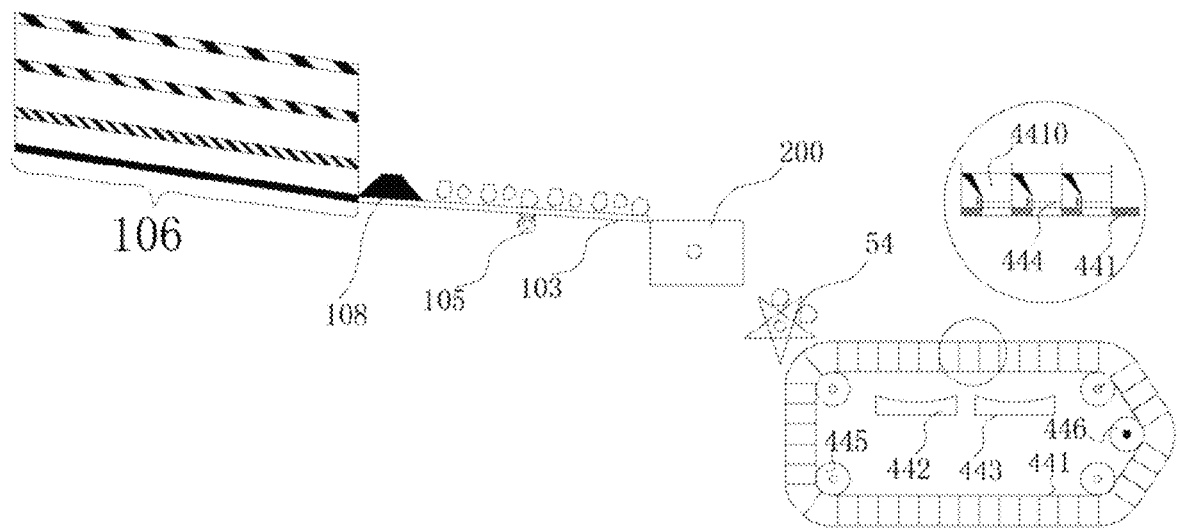
FIG. 25 is a top view of a multi-thread coal and gangue separation system provided by Embodiment 10.

Referring to FIG. 25, the present embodiment provides a linear coal and gangue separation device, including a transmission chain 441, a sixth conveying belt 442, and a seventh conveying belt 443. The transmission chain 441 is movably disposed, and the sixth conveying belt 442 and the seventh conveying belt 443 are disposed below the upper surface of the transmission chain 441 side by side.

The transmission chain 441 is provided with a chain slot 4410 used to be filled with a mineral aggregate; the bottom of the chain slot 4410 is provided with a second discharge electromagnetic valve 444 used to control discharge; and the second discharge electromagnetic valve 444 is used to control, according to an identification result on the mineral aggregate in the corresponding chain slot 4410, the chain slot 4410 to discharge the mineral aggregate to the sixth conveying belt 442 or the seventh conveying belt 443. For example, the sixth conveying belt 442 and the seventh conveying belt 443 are respectively a clean coal conveying belt and a gangue conveying belt; when the mineral aggregate in a certain chain slot 4410 is clean coal, and the chain slot 4410 moves to a position above the sixth conveying belt 442, the second discharge electromagnetic valve 444 corresponding to the chain slot 4410 is opened; and when the mineral aggregate in a certain chain slot 4410 is gangue, and the chain slot 4410 moves to a position above the seventh conveying belt 443, the second discharge electromagnetic valve 444 corresponding to the chain slot 4410 is opened.

In the present embodiment, a plurality of chain slots 4410 are arrayed on the transmission chain 441 to facilitate transportation of the mineral aggregate. Moreover, motion directions of the sixth conveying belt 442 and the seventh conveying belt 443 are perpendicular to a motion direction of the transmission chain 441 to facilitate coal and gangue separation relative to the motion directions of the chain slots 4410 by means of the sixth conveying belt 442 and the seventh conveying belt 443.

In the present embodiment, the highest plane where a motion trajectory of the transmission chain 441 is a horizontal plane; and carrying surfaces of the sixth conveying belt 442 and the seventh conveying belt 443 are located below the highest plane. Specifically, the present embodiment further includes a tension roller 446 and a fixed roller 445. The tension roller 446 and the fixed roller 445 are rotatably disposed and parallel to each other; the transmission chain 441 is arranged on the tension roller 446 and the fixed roller 445; and there are four fixed rollers 445 distributed to form a rectangle.

Referring to FIG. 25, in the present embodiment, a linear coal and gangue separation system is further provided, including a coal and gangue identification device 200 and the linear coal and gangue separation device in the present embodiment. The coal and gangue identification device 200 is used to identify a mineral aggregate; the sixth conveying belt 442 and the seventh conveying belt 443 are respectively used to convey clean coal and gangue; and the chain slot 4410 is used to accommodate the mineral aggregate identified by the coal and gangue identification device 200.

The linear coal and gangue separation system further includes a second transportation mechanism 54. The second transportation mechanism 54 is used to transport the mineral aggregate output by the coal and gangue identification device to the chain slot 4410 that is located at the highest plane of the motion trajectory of the transmission chain 441.

In the present embodiment, the coal and gangue identification device can use the coal and gangue identification device provided in embodiment 2, and the rotating wheel type coal and gangue identification device or photoelectric sorting device provided in embodiment 3.

Embodiment 10. Multi-Thread Coal and Gangue Separation System

Figure 26:
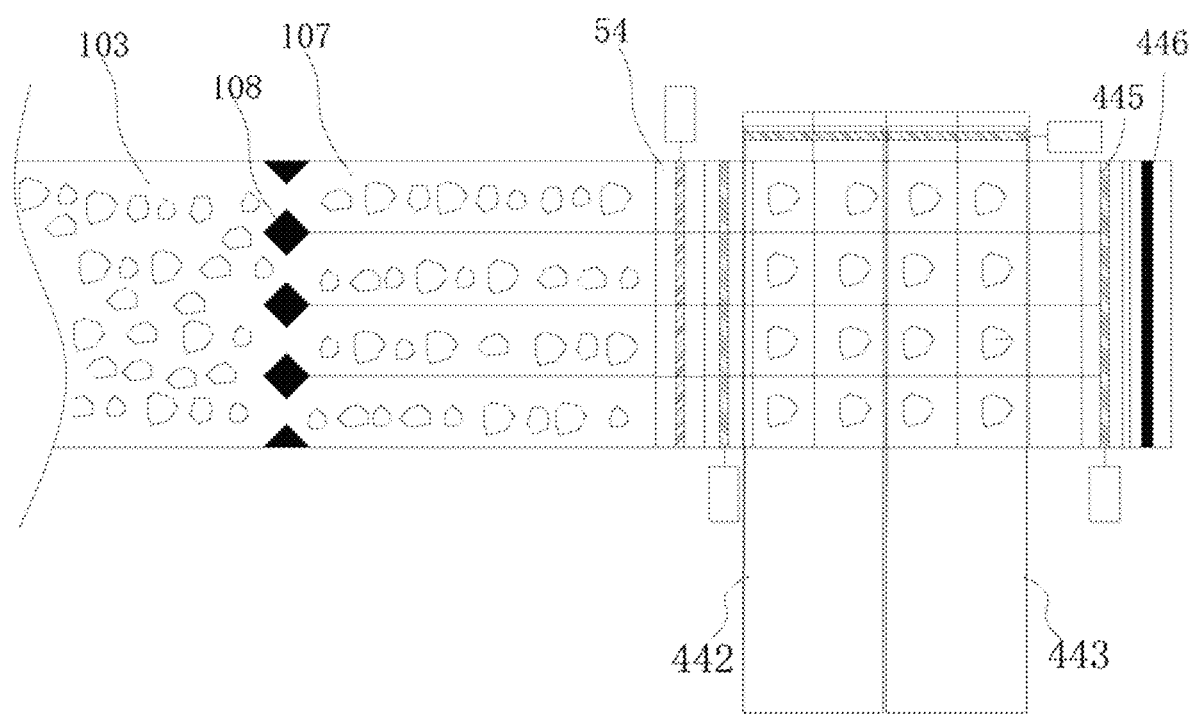
FIG. 26 is a top view of the system shown in FIG. 25.

Referring to FIG. 25 and FIG. 26, the present embodiment provides a multi-thread coal and gangue separation system, including a distribution queuing device 100, a coal and gangue identification device 200, and a coal and gangue separation device. The distribution queuing device 100 is used to respectively convey mineral aggregates according to particle size grades to the corresponding coal and gangue identification devices 200 for identification; and the coal and gangue separation device is used to convey, according to identification results, the mineral aggregate output by each coal and gangue identification device 200.

The coal and gangue separation device in the present embodiment uses the linear coal and gangue separation device provided in embodiment 9. The coal and gangue identification device 200 in the present embodiment uses the coal and gangue identification device provided in embodiment 2, and the rotating wheel type coal and gangue identification device or photoelectric sorting device provided in embodiment 3.

In the present embodiment, the distribution queuing device 100 includes a grading screen 106 and a discharge chute 103. The grading screen 106 is composed of a plurality of screen cloth with different apertures. The quantity of the screen cloth is equal to the quantity of the coal and gangue identification devices. The discharge chute 103 is used to convey the mineral aggregates screened by all the screen cloth to the corresponding coal and gangue identification devices 200. As such, different coal and gangue identification devices identify the mineral aggregates with the corresponding particle sizes to facilitate further improving the identification accuracy. In the present embodiment, the discharge chute 103 is provided with a sequencing runner 107; an inlet of the sequencing runner 107 is provided with a diversion and material separation structure 108; an outlet of the sequencing runner 107 faces the corresponding coal and gangue identification device; and the diversion and material separation structure 108 is of a flared structure, with the narrow end connected to the sequencing runner 107. As such, by means of the drainage of the diversion and material separation structure 108, it is ensured that the mineral aggregates orderly enter the sequencing runner 107, so as to orderly enter the coal and gangue identification devices, which is beneficial to preventing the mineral aggregates from blocking the discharge chute 103.

Referring to embodiment 1, in the present embodiment, the lower surface of the discharge chute 103 can also be provided with a shock excitation motor 105; the shock excitation motor 105 is configured to have relatively low shock excitation speed to guarantee full dispersion of the mineral aggregates; and when the mineral aggregates jump on the slot surfaces, the mineral aggregates can be kept to one side of the sequencing runner 107 and orderly line up to avoid overlapping of materials with small particle sizes.

In specific implementation, a plurality of discharge chutes 103 that are in one-to-one correspondence to the various coal and gangue identification devices can be arranged in the distribution queuing device 100. One or more sequencing runners that transport the mineral aggregates to the same coal and gangue identification device can be arranged on the various discharge chutes 103. In specific implementation, the distribution queuing device 100 can also be provided with one discharge chute 103. Sequencing runners 107 that are in one-to-one correspondence to the various coal and gangue identification devices are arranged on the discharge chute 103, so as to transport the mineral aggregates to the corresponding coal and gangue identification devices 200 by means of the various sequencing runners 107. In this implementation mode, it needs to ensure that the mineral aggregates at the various particle size grades and output by the grading screen 106 enter the corresponding diversion and material separation structures 108.

In specific implementation, the grading screen 106 can be arranged in the receiving hopper 101; outlets corresponding to the screen cloth with different apertures are formed in the receiving hopper 101; and the mineral aggregates at the corresponding particle size grades are conveyed to the corresponding discharge chutes 103 or the diversion and material separation structures 108 by means of the outlets. In the present embodiment, the plurality of screen cloth in the grading screen 106 are distributed from top to bottom according to the apertures from large to small. Specifically, as shown in FIG. 25, the grading screen 106 uses a multi-layer vibration grading screen, and the number of layers is set according to queuing and separation needs and the size of an alley space. In the present embodiment, a four-layer grading screen 106 can be arranged for a mineral aggregate of 25 to 300 mm. The partition particle size of each layer of screen cloth is [25-50 mm), [50-100 mm), [100-200 mm), and [200-300 mm].

In the present embodiment, a coal and gangue tracking unit and a control module are further included. The coal and gangue tracking unit is used to track and locate the mineral aggregates in the chain slots according to the identification results of the coal and gangue identification devices; and the control module controls, according to a tracking result of the coal and gangue tracking unit, the various second discharge electromagnetic valves 444 to work to ensure that the clean coal and the gangue in the chain slots 4410 are accurately discharged onto the sixth conveying belt 442 and the seventh conveying belt.

In the present embodiment, a second transportation mechanism 54 is further included. The second transportation mechanism 54 is used to transport the mineral aggregates output by the various coal and gangue identification devices to the corresponding chain slots 4410. The second transportation mechanism is composed of a plurality of star-type feeders arranged side by side; the plurality of star-type feeders respectively correspond to the plurality of coal and gangue identification devices; and rotating shafts of the plurality of star-type feeders are colinear and share the same driving motor. As such, the quantity of the star-type feeders is equal to the quantity of the coal and gangue identification devices and the quantity of chain slot arrays in a direction perpendicular to the transmission chain 441. By means of the star-type feeders, the mineral aggregates output by the coal and gangue identification devices are accurately conveyed to rows corresponding to the chain slot arrays.

The above only describes the preferred embodiments of the present invention, and is not intended to limit the present invention. Any modifications, equivalent replacements and improvements that are made within the spirit and principle of the present invention shall fall within the protection scope of the present invention.

What is claimed is:

1. A coal and gangue identification device, comprising a rotary supporting frame, a water injection unit, a weighing unit, a liquid level detection device, and a processing module, wherein the rotary supporting frame is provided with a loading unit used to load a mineral aggregate; the rotary supporting frame is used to drive the loading unit to rotate on a horizontal plane; in the rotating process of the rotary supporting frame, the loading unit cyclically passes through a water injection region (20a), a material adding region (20b), a volume measurement region (20c), and an unloading region (20d) which are sequentially disposed on a rotation trajectory of the rotary supporting frame; the water injection unit is used to inject water to the loading unit of the water injection region (20a);

the weighing unit is used to acquire the weight of the mineral aggregate filled to the loading unit in the material adding region (20b); the liquid level detection device is used to measure a liquid level in the loading unit on the volume measurement region (20c); the processing module is used to calculate, according to a measurement result of the liquid level detection device, a volume of the mineral aggregate filled to the loading unit, and is used to identify the mineral aggregate in combination with the volume and the weight of the mineral aggregate obtained by the weighing unit; and the processing module is also used to control, according to an identification result, the loading unit to perform unloading in the unloading region (20d).

2. The coal and gangue identification device according to claim 1, wherein the rotary supporting frame is provided with a plurality of loading units; the plurality of loading units are uniformly distributed in a rotation direction of the rotary supporting frame; each loading unit comprises at least one first weighing barrel (214); the bottom of each first weighing barrel (214) is provided with a first discharge electromagnetic valve (2112); and the first discharge electromagnetic valve (2112) is used to control the first weighing barrel (214) on the discharge region (20d) to perform discharge.

3. The coal and gangue identification device according to claim 2, wherein the rotary supporting frame comprises a first rotating shaft (217) that is vertically disposed, and a loading bracket that is connected with the first rotating shaft (217) and synchronously rotates with the first rotating shaft (217); and the various first weighing barrels (214) are arranged on the loading bracket.

4. The coal and gangue identification device according to claim 3, wherein the loading bracket comprises an upper supporting disk (212) and a lower supporting disk (213); the upper supporting disk (212) and the lower supporting disk (213) are both horizontally sleeved on the first rotating shaft (217) and are concentric with the first rotating shaft (217); the upper supporting disk (212) and the lower supporting disk (213) are provided with through holes corresponding to every first weighing barrel (214); and the through holes correspond to each other in a vertical direction and are used to fix the first weighing barrel (214).

5. The coal and gangue identification device according to claim 4, wherein the upper ends of the first weighing barrels (214) are provided with ring shaped overlap edges (2111) that extend to the outside; the weighing unit comprises a plurality of first weighing sensors (216) that are in one-to-one correspondence to the first weighing barrels (214); each first weighing sensor (216) is provided on the upper supporting disk (212); and the overlap edges of the first weighing barrels (214) are abutted against the corresponding first weighing sensors (216).

6. The coal and gangue identification device according to claim 1, further comprising a circulating water tank (201) and a dewatering screen (202), wherein the circulating water tank (201) is used to supply water to the water injection unit; the dewatering screen (202) is arranged above the circulating water tank (201) and located below the loading unit on the unloading region (20d); and the dewatering screen (202) is used to dewater the mineral aggregate discharged by the loading unit of the unloading region (20d).

7. The coal and gangue identification device according to claim 6, wherein a filtration division layer (2114) is arranged in the circulating water tank (201); the filtration division layer (2114) divides the circulating water tank (201) into a muddy water chamber (2011) and a clear water chamber (2012); the dewatering screen (202) is arranged above the muddy water chamber (2011); and the clear water chamber (2012) is used to supply water to the water injection unit.

8. The coal and gangue identification device according to claim 6, wherein the water injection unit comprises a first metering pump (2113) and a sprayer that is used to inject water to the first weighing barrel (214) of the water injection region (20a); and the sprayer is communicated with the circulating water tank (201) by means of the first metering pump (2113).

9. A coal and gangue sorting system, comprising a coal and gangue sorting device, and further comprising the coal and gangue identification device according to claim 1, wherein the coal and gangue sorting device comprises a second conveying belt (431); a feeding end of the second conveying belt (431) is located below the unloading region (20d); a gangue runner and a clean coal runner are arranged on the second conveying belt (431) side by side; and the processing module of the coal and gangue identification device is used to control, according to an identification result, the loading unit to discharge the mineral aggregate to the clean coal runner or the gangue runner in the unloading region (20d).

10. The coal and gangue sorting system according to claim 9, wherein the second conveying belt (431) is provided with a runner partition plate (432) in a motion direction of the second conveying belt; the runner partition plate (432) is used to partition two opposite sides of the second conveying belt (431) into a gangue runner and a clean coal runner; the coal and gangue identification device further comprises a circulating water tank (201) and a dewatering screen (202); the circulating water tank (201) is used to supply water to the water injection unit; the dewatering screen (202) is arranged above the circulating water tank (201) and is located below the loading unit located on the unloading region (20*d*); the dewatering screen (202) is used to convey a material discharged by the loading unit on the unloading region (20*d*) to the second conveying belt (431); and the dewatering screen (202) is provided with a middle partition plate to partition the dewatering screen (202) into both sides respectively corresponding to the clean coal runner and the gangue runner.

* * * * *